United States Patent
Benderly et al.

(10) Patent No.: US 8,705,018 B2
(45) Date of Patent: Apr. 22, 2014

(54) ARRANGEMENT FOR AND METHOD OF EXAMINING GEMSTONES

(75) Inventors: David Benderly, New York, NY (US); Jason Ian VanAnden, Brooklyn, NY (US); David Liatti, Brooklyn, NY (US)

(73) Assignee: Photoscribe, Inc., New York, NY (US)

( * ) Notice: Subject to any disclaimer, the term of this patent is extended or adjusted under 35 U.S.C. 154(b) by 321 days.

(21) Appl. No.: 13/026,531

(22) Filed: Feb. 14, 2011

(65) Prior Publication Data

US 2011/0206234 A1  Aug. 25, 2011

Related U.S. Application Data

(60) Provisional application No. 61/308,062, filed on Feb. 25, 2010.

(51) Int. Cl.
*G01N 21/00* (2006.01)
*G01N 21/55* (2006.01)

(52) U.S. Cl.
USPC ............................................. 356/30; 356/445

(58) Field of Classification Search
USPC ............................................ 356/30, 402–425
See application file for complete search history.

(56) References Cited

U.S. PATENT DOCUMENTS

| | | | |
|---|---|---|---|
| 3,980,890 A * | 9/1976 | Heckrodt et al. ........ 250/559.28 | |
| 4,259,011 A | 3/1981 | Crumm | |
| 4,291,975 A | 9/1981 | Raccah | |
| 4,394,580 A | 7/1983 | Gielisse | |
| 4,652,913 A | 3/1987 | Saitoh | |
| 4,906,093 A | 3/1990 | Trossarelli | |
| 5,118,181 A | 6/1992 | Yifrach | |
| 5,124,935 A | 6/1992 | Wallner | |
| 5,148,288 A | 9/1992 | Hannah | |
| 5,164,586 A | 11/1992 | Hohberg | |
| 5,237,407 A | 8/1993 | Crezee | |
| 5,615,005 A | 3/1997 | Valente | |
| 5,828,405 A | 10/1998 | Vanier | |
| 6,020,954 A | 2/2000 | Aggarwal | |
| 6,239,867 B1 | 5/2001 | Aggarwal | |
| 6,304,853 B1 | 10/2001 | Malnekoff | |
| 6,348,964 B1 | 2/2002 | Wagner | |
| 6,473,164 B1 | 10/2002 | De Jong | |
| 6,786,733 B2 | 9/2004 | Lapa | |
| 6,813,007 B2 | 11/2004 | Lapa | |
| 6,980,283 B1 * | 12/2005 | Aggarwal ........................ 356/30 |
| 7,239,739 B2 | 7/2007 | Lapa | |

(Continued)

OTHER PUBLICATIONS

Pala International, http://www.palagems.com/quality_4cs.htm.*

*Primary Examiner* — Gregory J Toatley
*Assistant Examiner* — Hina F Ayub
(74) *Attorney, Agent, or Firm* — Kirschstein, et al.

(57) ABSTRACT

An arrangement for, and a method of, accurately determining at least one optical property, such as coverage and/or symmetry, of a gemstone, employ an energizable, stationary light source for directing light rays at different orientations to an uncovered table of the gemstone, and an energizable, stationary backlight spaced away from a culet of the gemstone. A controller energizes the light source to generate return light from the gemstone for each light ray, and energizes the backlight to illuminate the gemstone from behind. An imager images the return light as a plurality of frontlit images, and images the backlit gemstone as a backlit image. The controller processes at least one of the images to determine the optical property of the gemstone.

12 Claims, 10 Drawing Sheets

(56) References Cited

U.S. PATENT DOCUMENTS

| | | |
|---|---|---|
| 7,260,544 B1 | 8/2007 | Reinitz |
| 7,701,569 B2 * | 4/2010 | Yang .................. 356/237.2 |
| 2004/0218391 A1 | 11/2004 | Procter |
| 2005/0069858 A1 | 3/2005 | Lapa |
| 2005/0151959 A1 * | 7/2005 | Geurts .................. 356/30 |
| 2005/0213077 A1 | 9/2005 | Sasian |
| 2006/0074588 A1 | 4/2006 | Blodgett |
| 2006/0164623 A1 | 7/2006 | Wagner |
| 2007/0038530 A1 | 2/2007 | Wagner |
| 2007/0109529 A1 | 5/2007 | Wagner |
| 2007/0132983 A1 | 6/2007 | Van de Velde |
| 2007/0136085 A1 | 6/2007 | Wagner |
| 2008/0055582 A1 * | 3/2008 | Lapa et al. .................. 356/30 |
| 2008/0231833 A1 | 9/2008 | Shlezinger |
| 2009/0079987 A1 * | 3/2009 | Ben-Ezra et al. ............. 356/445 |
| 2011/0170291 A1 * | 7/2011 | Simon .................. 362/241 |
| 2011/0228063 A1 * | 9/2011 | Smith et al. .................. 348/61 |
| 2012/0147359 A9 * | 6/2012 | Stetten et al. .................. 356/73 |

* cited by examiner

ARRANGEMENT FOR AND METHOD OF EXAMINING GEMSTONES

CROSS REFERENCE TO RELATED APPLICATION

This application claims the benefit of U.S. Provisional Patent Application Ser. No. 61/308,062, filed Feb. 25, 2010.

BACKGROUND OF THE INVENTION

The present invention generally relates to an arrangement for, and a method of, examining gemstones, especially cut diamonds, by illuminating the gemstone, capturing images of the illuminated gemstone, and analyzing the captured images with repeatability.

The beauty and price of a gemstone, such as a cut multi-faceted diamond, are based, for example, on its cut, carat weight, clarity and color. Many different geometrical patterns of cuts, such as round brilliant, oval, pear, marquise, radiant, princess, heart, emerald, etc. are now standardized. The cut, the carat weight, the clarity and the color of the gemstone are typically evaluated and/or measured by a human appraiser. Such evaluated and/or measured properties are often objectively presented to a consumer, typically in certificate form, for price valuation.

Optical performance of the gemstone, that is, how the gemstone "plays with light", as well as optical efficiency, that is, how the gemstone "reflects light", are difficult to subjectively evaluate and measure, even for the experienced human appraiser. Optical performance and efficiency of the gemstone are typically characterized by such properties as its brilliance (the amount and intensity of incident light returned from the gemstone), scintillation (fast and local fluctuations in the incident light returned as the gemstone moves), fire (the dispersion of incident white light into its spectral colors), coverage (the area of the incident light returned compared to the total area of the gemstone table), contrast (the intensity of the incident white light returned compared to the intensity of the non-returned or black light), and symmetry (the balance of the pattern of the incident light returned). A more visually active gemstone is deemed more valuable than a less visually active gemstone, even with the same cut, carat weight, clarity and color.

To objectively measure such optical properties of gemstones, the art has disclosed various computer-based systems for capturing and analyzing images of gemstones illuminated under varying lighting conditions. For example, U.S. Pat. No. 5,615,005 discloses a gemstone evaluation system that captures images of a gemstone placed table-side face-down on a glass plate in an analysis chamber and illuminated from a plurality of different angles by a movable light source that is moved toward the gemstone during the evaluation. Captured images of the gemstone are analyzed by a computer, and various optical properties of the gemstone are measured and displayed or printed.

As another example, U.S. Pat. No. 6,813,007 discloses another computer-based system that captures images of a gemstone also placed table-side face-down on a glass plate, but illuminated by light reflected off a rotary reflector that rotates during the evaluation. Captured images of the gemstone are again analyzed by a computer, and various optical properties of the gemstone are measured and displayed or printed.

However, as advantageous as such computer-based systems have been, they have not proven to be altogether satisfactory in use. A moving system component, such as a rotating reflector or a moving light source, causes mechanical variability and vibrations that can interfere with the measurements, and degrade measurement accuracy and repeatability. The light source also concomitantly generates heat that can interfere with the measurements. Also, the glass plate on which the gemstone is placed creates an interface at which light interference can occur due to light refraction, thereby again degrading measurement accuracy and repeatability. This interference effect is aggravated by frequent contamination with dust, dirt, oil from an operator's fingers, scratches, or like contaminants on the glass plate. Furthermore, the placement of the gemstone on the glass plate is variable, thereby still further worsening measurement accuracy and repeatability. An objective, accurate and repeatable examination of a gemstone is essential for true price valuation of the gemstone.

SUMMARY OF THE INVENTION

One aspect of this invention is directed to an arrangement for accurately examining, with repeatability, one or more optical properties such as coverage and/or symmetry of a gemstone, especially a cut, multi-faceted diamond having a table (i.e., the uppermost, largest facet at the top of the diamond) and a culet (i.e., the pointed or blunted bottom of the diamond). An energizable, stationary light source is spaced away from the gemstone and is operative for directing light rays at different orientations to the table of the gemstone when energized.

In one embodiment, the stationary light source comprises a plurality of light sources spaced along an axis away from, and facing, the table of the gemstone, for directly directing the light rays at the different orientations to the table of the gemstone. Each light source preferably comprises a multitude of light-emitting elements, such as light emitting diodes, arranged in an annulus around the axis, with each annulus having a different diameter. A support, preferably annular in shape, is advantageously provided for supporting the light sources at different axial distances away from the gemstone. An optional homogenizer may be provided and supported by the support for homogenizing and making more uniform the light from each light source directed to the gemstone.

In another embodiment, a support is spaced from the light source, for supporting a plurality of light reflectors of different reflectivity, e.g., different colors of the light spectrum, and at different angular orientations and distances along an axis away from the table of the gemstone. Each light reflector is preferably arranged in an annulus around the axis, each annulus having a different diameter. The stationary light source, preferably a plurality of light emitting diodes lying in a plane, emits uniform light for reflection simultaneously from all the light reflectors as the light rays at the different orientations directly to the table of the gemstone.

An energizable stationary backlight is oppositely positioned from either support to face the culet of the gemstone. The backlight lies in a plane and uniformly illuminates the gemstone when energized. The backlight could also comprise multiple light emitting diodes arranged in a two-dimensional array, preferably overlaid with a light homogenizer.

A controller or microprocessor, preferably a programmed computer, is operative for energizing the light source to generate return light from the gemstone for each light ray, as well as for energizing the backlight to illuminate the gemstone from behind. The controller advantageously controls a power supply that supplies the voltages for energizing the light source and the backlight. In an advantageous embodiment, the backlight is energized first, and then the light source is energized. When a plurality of light sources is employed, they are individually energized, preferably, but not necessarily, in an ordered sequence.

A solid-state imager is spaced along an axis away from the gemstone, and preferably has a two-dimensional array of cells or photosensors, which correspond to image elements or pixels in a field of view of the imager. An optical focusing lens assembly is provided for capturing the return light from the gemstone and the light in the field of view of the backlit gemstone, and for projecting the captured light onto the imager during an exposure time period. The imager may be a charge coupled device (CCD) or a complementary metal oxide semiconductor (CMOS) device, together with associated integrated bandpass spectral filters and electronic circuits for producing electrical signals corresponding to a two-dimensional array of pixel information over the field of view, and is similar to that used in a digital camera. The imager is operative for imaging the return light from the light rays as a plurality of frontlit images, and for imaging the light in the field of view of the backlit gemstone as a backlit image.

The controller is further operative, as described in detail below, for processing at least one of the frontlit images and the backlit image, to determine the coverage and/or symmetry properties of the gemstone. Other optical properties that can be determined are the aforementioned contrast, fire, brilliance and scintillation.

The arrangement advantageously also comprises one or two position adjusters for axially adjusting a position of the imager and/or the light source relative to each other and the gemstone. A gemstone holder or fixture is operative for holding and automatically positioning the gemstone in a predetermined upright position in which the table of the gemstone is uncovered and directly exposed to each light ray. A support plate, preferably of rigid material, commonly mounts the light source, the backlight, the imager and the gemstone holder. Shock-absorbers on the support plate are employed for resisting shock forces from reaching the light source, the backlight, the imager and the gemstone holder. Such forces can originate from the environment exterior to the arrangement, or from the interior, for example, from cooling fans within the power supply, also mounted on the support plate.

Still another aspect of this invention is directed to a method of examining at least one property, such as coverage and/or symmetry, as well as other optical properties, of the gemstone. The method is performed by directing light rays at different angular orientations to the gemstone by energizing a stationary light source to generate return light from the gemstone for each light ray, imaging the return light as a plurality of frontlit images, and processing at least one of the frontlit images.

The method is further performed by directing the light rays to an uncovered table of the gemstone, and by positioning an energizable stationary backlight to face a culet of the gemstone. The backlight is energized to illuminate the gemstone from behind. The light in the field of view of the backlit gemstone is imaged as a backlit image. The backlit image is processed, preferably together with the at least one frontlit image, to determine one or more optical properties of the gemstone.

As a preferred initial step, the backlit image is processed to determine a silhouette or outline of the backlit gemstone, and a number of total pixels is counted within an area or region of interest of the gemstone. Symmetry is advantageously determined by processing each frontlit image of the return light, generating virtual images mirror symmetrical to the frontlit images, counting a number of symmetrical pixels common to each frontlit image and its respective virtual image within the area of the gemstone, and analyzing the counted number of symmetrical pixels compared to the number of total pixels. Coverage is advantageously determined by counting a number of coverage pixels having an intensity above a predetermined value in coverage regions of the backlit image within the area of the gemstone, and analyzing the number of coverage pixels compared to the number of total pixels.

Thus, the arrangement of this invention has no rotating light reflectors or moving light sources, as in the prior art, that could cause mechanical variability and vibrations to interfere with the measurements, and thereby degrade measurement accuracy and repeatability. The light emitting diodes of this invention are stationary and are relatively cool-running devices that do not generate heat, as in the prior art, to interfere with the measurements. Rather than moving the light incident on the gemstone, the spaced-apart light sources in one embodiment are energized, one at a time, or the light reflectors in another embodiment simultaneously reflect light incident thereon, thereby obtaining multiple frontlit images to be processed. The arrangement of this invention does not place the gemstone table-side face-down on a glass plate and thus avoids light interference effects, as in the prior art, due to light refraction from a covered table. The arrangement of this invention holds the gemstone in a predetermined, upright position in which the table is uncovered and directly exposed to the light rays. The lack of a glass plate means that no contamination can occur due to dust, dirt, oil from an operator's fingers, scratches, or like contaminants. The arrangement of this invention provides an objective, accurate and repeatable examination of the coverage and symmetry properties of a gemstone essential for true price valuation of the gemstone.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE PREFERRED EMBODIMENTS

Figure 1:
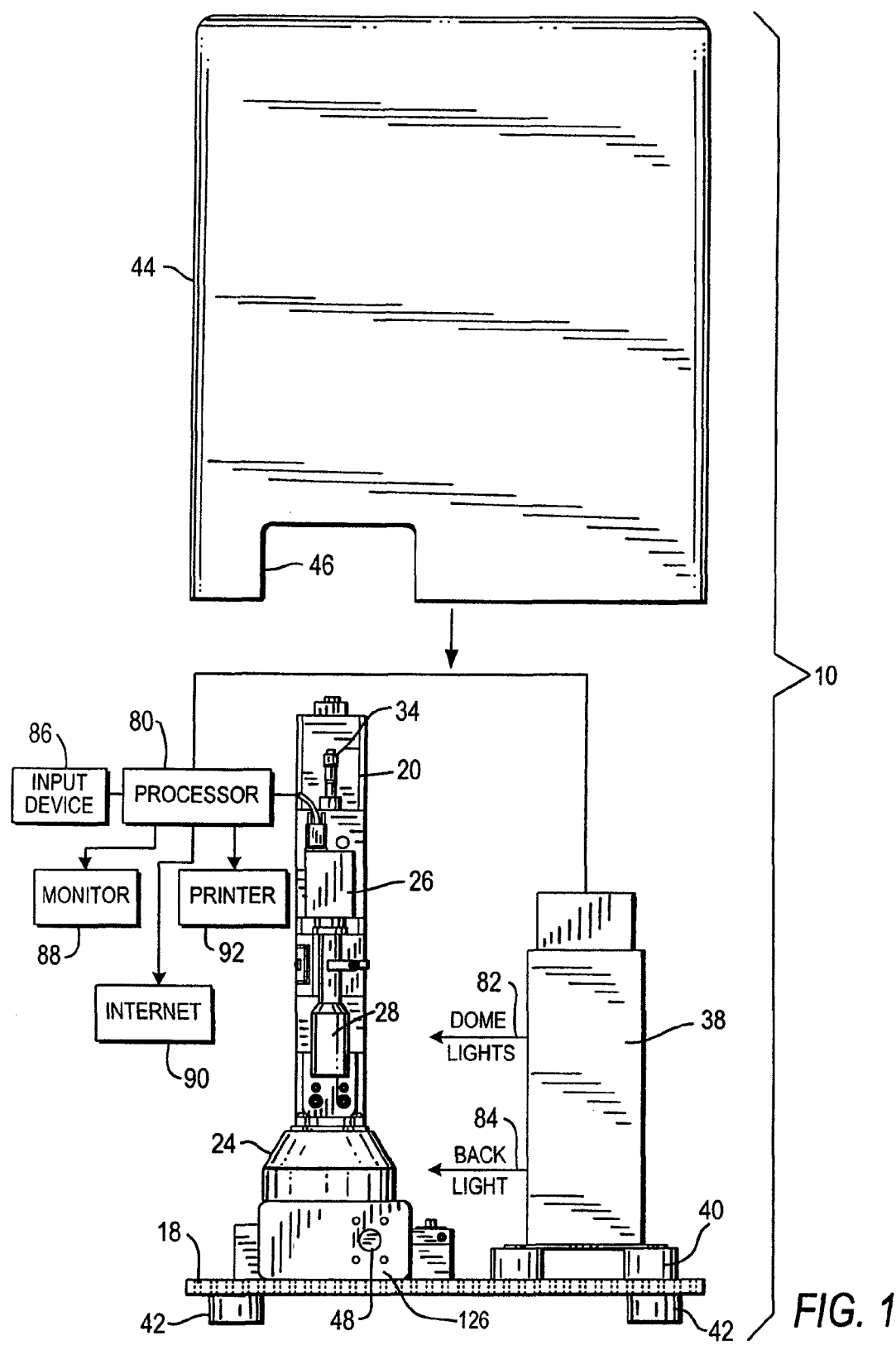
FIG. 1 is an exploded, front elevational view of an arrangement for accurately determining at least one optical property, such as symmetry and/or coverage, of gemstones in accordance with the method of this invention.
Figure 3:
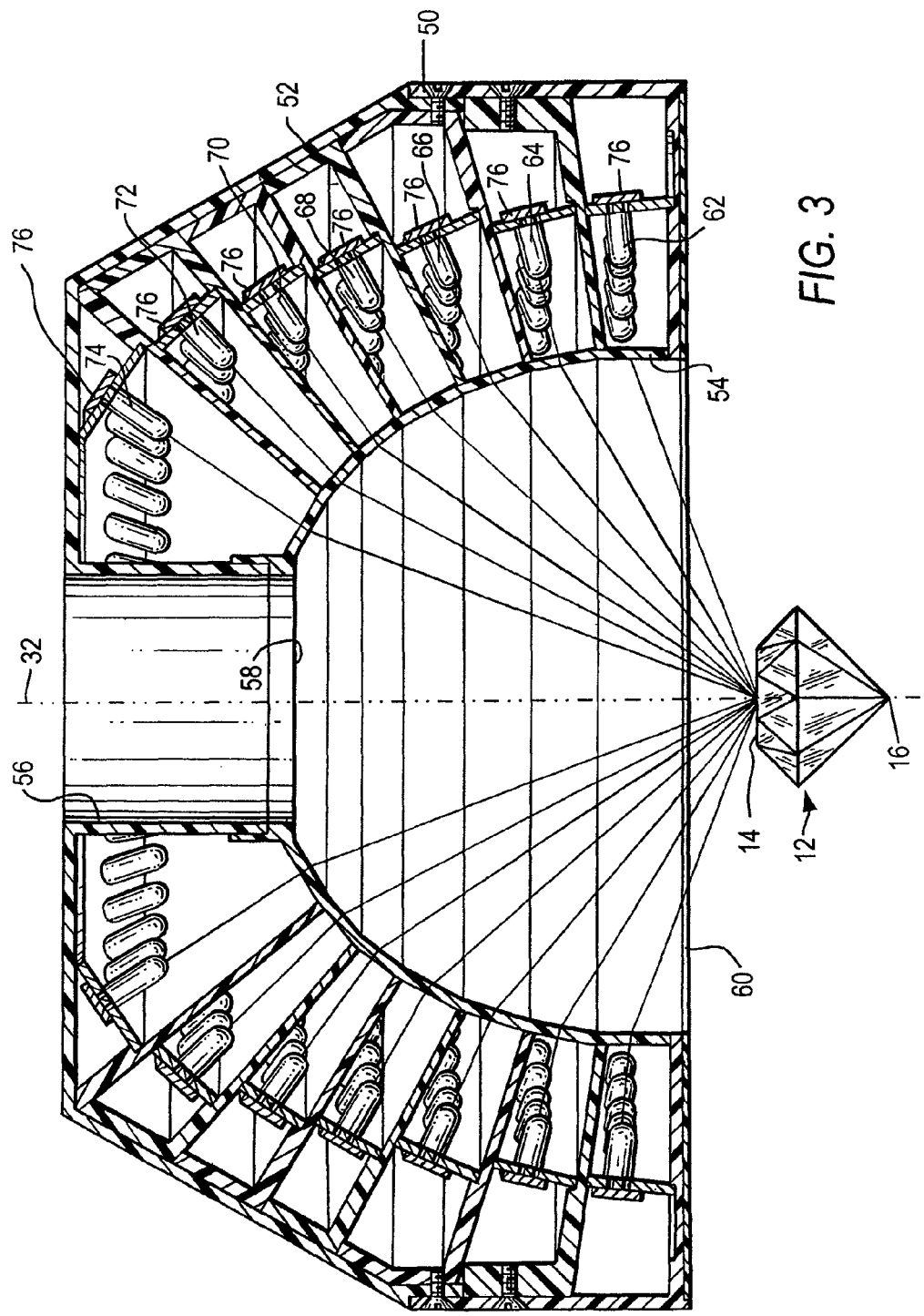
FIG. 3 is an enlarged, sectional view of one embodiment of an annular support for supporting a plurality of light sources facing a table of a gemstone, as employed in the arrangement of FIG. 1.

Referring now to FIG. 1 of the drawings, reference numeral 10 generally identifies an arrangement for accurately determining, with repeatability, one or more optical properties such as coverage and/or symmetry of a gemstone 12, especially a cut, multi-faceted diamond having, as best shown in FIG. 3, a table 14 (i.e., the uppermost, largest facet at the top of the diamond) and a culet 16 (i.e., the pointed or blunted bottom of the diamond). Although FIG. 3 depicts that the gemstone 12 has a round cut, the arrangement 10 is equally applicable for determining the coverage and/or symmetry of gemstones having other cuts, such as oval, pear, marquise, radiant, princess, heart, emerald, etc.

Figure 2:
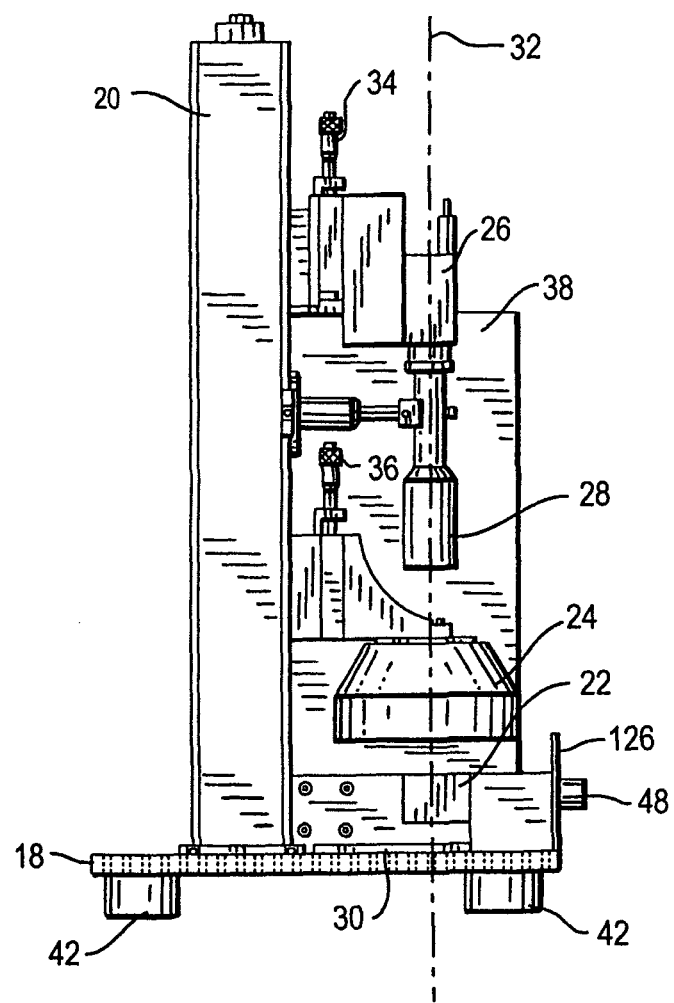
FIG. 2 is a side elevational view of part of the arrangement of FIG. 1, with a cover removed.

As shown in FIGS. 1-2, the arrangement 10 includes a horizontal support plate 18, preferably of rigid material, on which an upright, vertical standard 20 is mounted. A gemstone holder 22 or fixture, as best shown in FIGS. 4-11, is mounted on the support plate 18 behind a drawer front panel 126 and is operative, as described below, for holding and automatically positioning the gemstone 12 in a predetermined upright position. An annular support 24, as best shown in FIG. 3, is mounted on the standard 20 above the gemstone holder 22. In the embodiment of FIG. 3, the annular support 24 is operative, as described below, for supporting a plurality of light sources that face the table 14 of the gemstone 12 in the holder 22. In an alternate embodiment, as described below in connection with FIG. 14, a different annular support is operative for supporting a plurality of light reflectors that face the table 14 of the gemstone 12 in the holder 22. A backlight 30 is mounted on the support plate 18 and faces the culet 16 of the gemstone 12 in the holder 22.

A solid-state imager 26 is also mounted on the standard 20 above the annular support 24 and is operative, as described below, for imaging light returning from the gemstone 12. An optical focusing lens assembly 28 is also mounted on the standard 20 between the annular support 24 and the imager 26, and is operative for capturing the light returning from the gemstone, and for projecting the captured light onto the imager 26 during an exposure time period. The imager 26, the lens assembly 28, the annular support 24, the gemstone 12 and the backlight 30 are all aligned along an optical path or axis 32 that is parallel to the elongation of the vertical standard 20.

A first position adjuster 34 is operative for axially adjusting a position of the imager 26 and the lens assembly 28 along the optical path 32 relative to the gemstone 12. A second position adjuster 36 is operative for axially adjusting a position of the annular support 24 along the optical path 32 relative to the gemstone 12. A power supply 38 is mounted on the support plate 18 and is operative, as described below, for supplying power to the light sources in the annular support 24 and to the backlight 30. Shock absorbers 40 between the power supply 38 and the support plate 18, as well as shock absorbers or feet 42 on the bottom of the support plate 18, are employed for resisting shock forces from reaching the light sources, the backlight 30, the imager 26, the lens assembly 28 and the gemstone holder 22. Such forces can originate from the environment exterior to the arrangement 10, or from the interior, for example, from cooling fans within the power supply 38. A cover 44 is removably mounted over the components mounted on the support plate 18 and on the standard 20. The cover 44 has a cutout 46 to provide access to a handle 48 on the drawer front panel 126, and clearance for the latter.

As shown in FIG. 3, the annular support 24 has a cylindrical lower housing portion 50 and a frustoconical upper housing portion 52, together resembling a domed structure symmetrical about the axis 32. The upper housing portion 52 has an axial passage 56 through which light passes en route to the imager 26. An optional dome-like homogenizer 54 of light-homogeneous material may be provided within the annular support 24 and has opposite openings 58, 60 through which light passes.

A plurality of energizable, stationary light sources 62, 64, 66, 68, 70, 72, 74 is supported by the annular support 24 and spaced along the axis 32 at different axial distances away from, and facing, the table 14 of the gemstone 12. Each light source 62, 64, 66, 68, 70, 72, 74 comprises a multitude of light-emitting elements, such as light emitting diodes (LEDs), arranged in an annulus around the axis 32, with each annulus having a different diameter. In a preferred embodiment, there are seven annular light sources, and each annular light source comprises about fifty to seventy LEDs mounted on respective annular flexible circuit boards 76. Each LED is operative for emitting light rays to the gemstone when energized. More or fewer than seven annular light sources could be employed. More or fewer than fifty to seventy LEDs may comprise each annular light source. Advantageously, the LEDs are preselected such that their individual output powers are substantially the same. When energized, each annular light source generates a light ray in an annular zone of generally uniform illumination, but at a different angular orientation relative to, as well as a different axial distance from, the gemstone 12.

As noted above, the energizable stationary backlight 30 faces the culet 16 of the gemstone 12, lies in a plane and uniformly illuminates the gemstone from behind when energized. The backlight 30 also comprise multiple LEDs arranged in a two-dimensional array, preferably overlaid with a planar light homogenizer of light-homogeneous material. When energized, the backlight 30 generates a planar zone of homogenized light of generally uniform illumination behind the gemstone 12.

A controller 80 (see FIG. 1) or microprocessor, preferably a programmed computer, is operatively connected to the power supply 38, and is operative for individually energizing the light sources 62, 64, 66, 68, 70, 72, 74 to generate return light from the gemstone 12 for each light source in the annular support, as well as for energizing the backlight 30 to illuminate the gemstone 12 from behind. The power supply 38 has an output 82 that supplies the voltages for energizing the light sources, and an output 84 that supplies the voltage for energizing the backlight 30. The electrical wiring between the power supply 38 the light sources and the backlight 30 are not shown for clarity. In an advantageous embodiment, the backlight 30 is energized first, and then the plurality of light sources 62, 64, 66, 68, 70, 72, 74 is energized, preferably, but not necessarily, in an ordered sequence, e.g., from the closest to the furthest annular light source.

As noted above, the solid-state imager 26 is spaced along the axis 32 away from the gemstone 12, and preferably has a two-dimensional array of cells or photosensors, which correspond to image elements or pixels in a field of view of the imager. The optical focusing lens assembly 28 is operative for capturing the return light from the gemstone 12 and the light in the field of view of the backlit gemstone 12, and for projecting the captured light onto the imager 26 during an exposure time period. The imager 26 may be a charge coupled device (CCD) or a complementary metal oxide semiconductor (CMOS) device, together with associated integrated spectral filters and electronic circuits for producing electrical signals corresponding to a two-dimensional array of pixel information over the field of view, and is similar to that used in a digital camera. The imager 26 is operative for imaging the return light from the gemstone 12 from each light source through the passage 56 as a plurality of frontlit images, and for imaging the light in the field of view of the backlit gemstone 12 through the passage 56 as a backlit image. The frontlit images represent different images of the gemstone taken at different relative orientations and/or distances between the gemstone and the light source and simulate the effect of a moving light source, but without the above-described drawbacks thereof.

The controller 80 is further operative, as described in detail below, for processing the backlit and the frontlit images, to determine the symmetry and/or coverage of the gemstone 12. The controller 80 is located exteriorly of the arrangement outside the cover 44, but could be incorporated within the cover. Input data can be input to the controller 80 via an input device 86, e.g., a mouse, keyboard, joystick, etc. Measurement data can be output from the controller 80 via an output device, e.g., a monitor 88, a printer 92, an internet connection 90, etc.

As noted above, the gemstone holder 22 or fixture is operative for holding and automatically positioning the gemstone 12 in a predetermined upright position in which the table 14 of the gemstone 12 is uncovered (see FIG. 3) and directly exposed to the light from each annular light source 62, 64, 66, 68, 70, 72, 74. In the predetermined upright position, the light from each LED enters the gemstone 12 slightly below the table 14 to minimize any specular reflections off the table 12. In the predetermined upright position, the table 14 of the gemstone 12 is preferably slightly above a top surface 128 of the holder 22.

Figure 5:
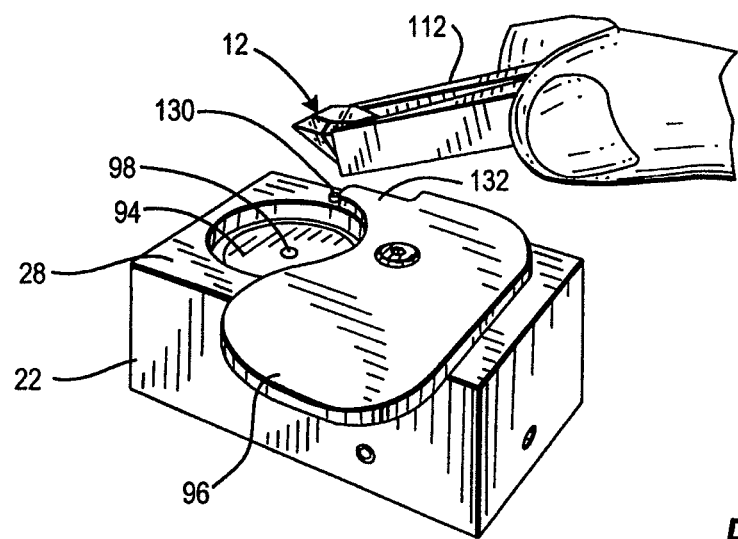
FIG. 5 is a perspective view of the gemstone holder of FIG. 4 during loading of the gemstone.
Figure 6:
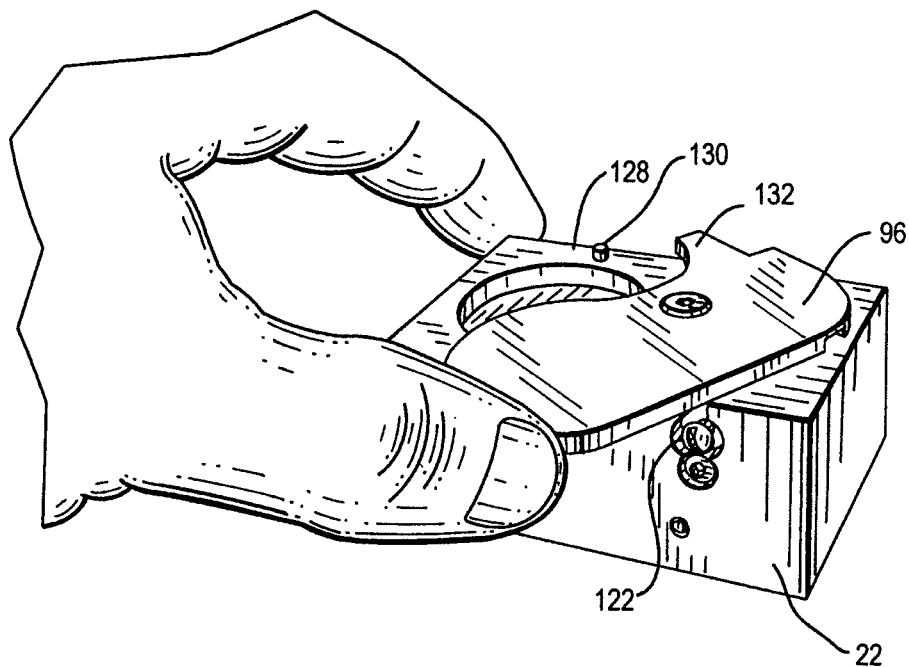
FIG. 6 is a perspective view of the gemstone holder of FIG. 5 after loading of the gemstone.
Figure 7:
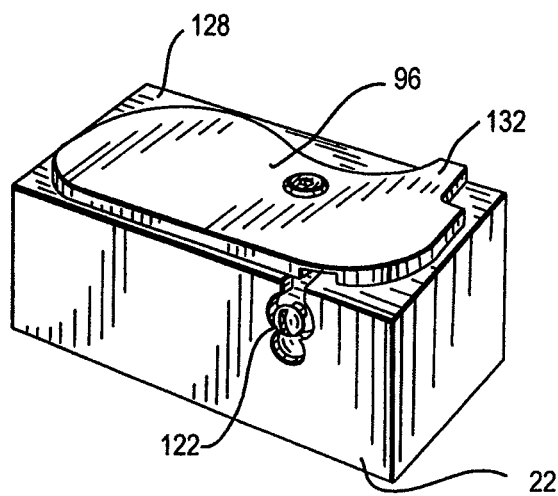
FIG. 7 is a perspective view of the gemstone holder of FIG. 6 ready to be placed in the arrangement of FIG. 1.
Figure 10:
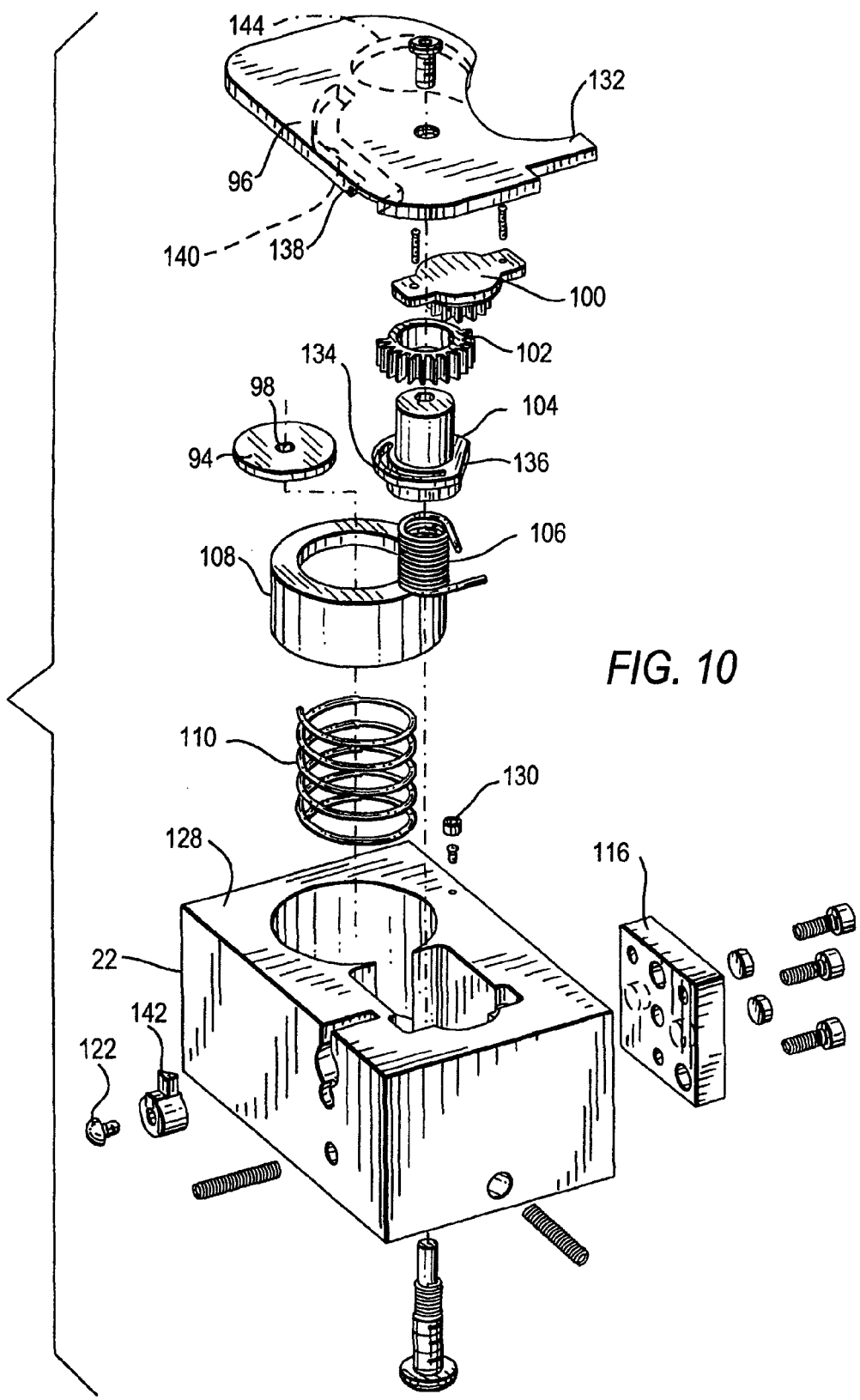
FIG. 10 is an exploded, perspective view of parts of the gemstone holder of FIG. 4.

As depicted in FIGS. 4-7, the gemstone holder 22 includes a protective lid 96 pivotably mounted on the gemstone holder 22 for movement between an open position (FIG. 5) and a closed position (FIG. 7). A stop 130 is mounted on the holder 22 and extends above the top surface 128 to abut against an extension 132 of the lid 96 to define the open position. A shoulder 138 (see FIG. 10) formed in a curved recess 140 on the underside of the lid 96 abuts against a lock 142 that extends above the top surface 128 to define the closed position. A release 122 releases the lock 142 when depressed. FIG. 10 depicts a stationary gear 100 fixed to the holder 22. Gear 100 meshes with sector gear 102 that is mounted on a spindle 104 that is jointly movable with the lid 96. A tensionable spring 106 is connected to the lid 96 via the spindle 104. The spindle 104 has a curved surface 134 and a flat surface 136. The spring 106 acts to constantly bias the lid 96 to the open position. The gears 100, 102 act to slow the rate at which the lid 96 is moved to the open position by the spring 106.

Figure 4:
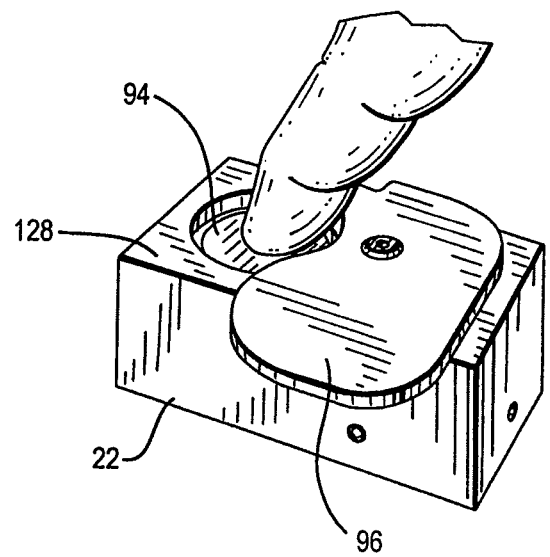
FIG. 4 is a perspective view of a gemstone holder being prepared to receive a gemstone, prior to being placed in the arrangement of FIG. 1.

In FIG. 4, an operator has already manually depressed the release 122 and released the lock 142 from the shoulder 138, thereby enabling the tensioned spring 106 to pivot the lid 96 until it is held in the illustrated open position by mutual engagement between the stop 130 and the extension 132. During this pivoting movement, the lock 142 passes with clearance along the curved recess 140 in the lid 96. A mounting plate 94 having a hole 98 therein (see FIG. 5) is exposed in the open position. FIG. 10 depicts a flanged sleeve 108 that holds the mounting plate 94 against the restoring force of a return spring 110. The mounting plate 94 and the sleeve 108 are jointly movable up-and-down. In FIG. 4, the operator pushes the mounting plate 94 down, where it is latched in the down position by mutual frictional engagement between the sleeve 108 and the curved surface 134 of the spindle 104.

In FIG. 5, the operator loads the gemstone 12 into the hole 98 of the mounting plate 94. Holes 98 of different sizes and mounting plates 94 of different heights can be used to accommodate differently sized gemstones. Tweezers 112 or gloves are recommended to avoid contamination. In FIG. 6, the operator pivots the lid 96 against the force of the spring 106 to the closed position until the lock 142 lockingly engages the shoulder 138. This action turns the spindle 104 until the flat surface 136 faces the sleeve 108, thereby unlatching the sleeve 108 and the mounting plate 94, both of which are released and move up under the force of the spring 110. In FIG. 7, the table 14 of the gemstone 12 is pressed against the underside of the closed lid 96 inside and against an inner wall of another curved recess 144 (see FIG. 10) due to the force of the spring 110. This is the aforementioned predetermined upright position of the gemstone 12, which is repeatable for the same gemstone, as well as from one gemstone to the next. The table 14 is positioned in a plane slightly above the top surface 128 of the holder 22. The gemstone holder 22 with its pre-positioned gemstone 12 is now ready to be placed in the arrangement 12.

Figure 8:
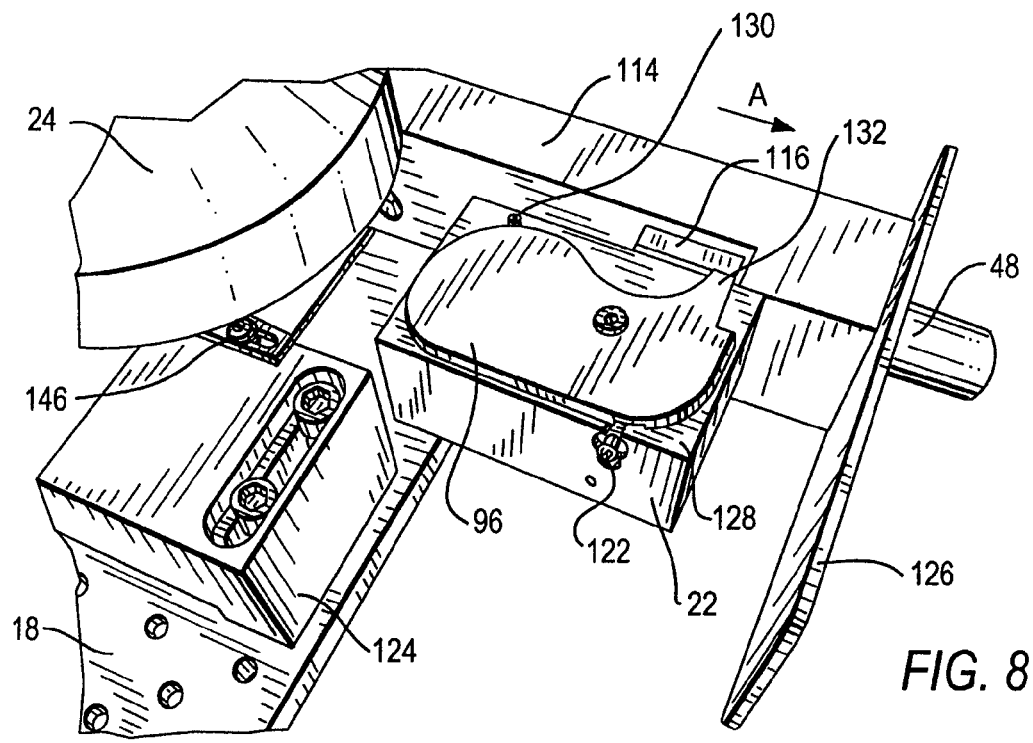
FIG. 8 is a broken-away, perspective view of the gemstone holder of FIG. 7 placed in an open drawer of the arrangement of FIG. 1.
Figure 11:
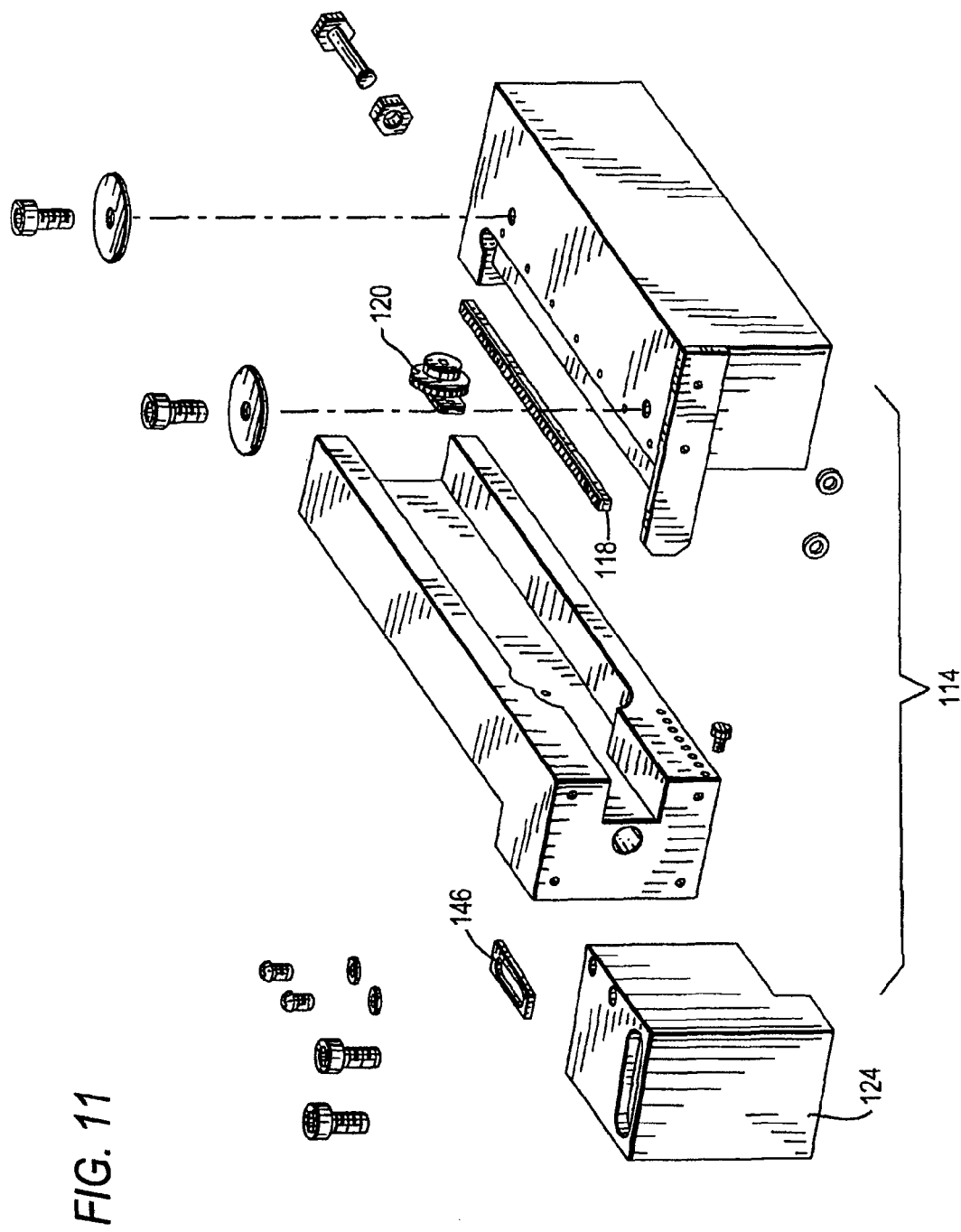
FIG. 11 is an exploded, perspective view of parts of the drawer of FIG. 8.

In FIG. 8, a drawer 114 is pulled out in the direction of the arrow A by the handle 48, and the gemstone holder 22 with its pre-positioned gemstone 12 is placed in the drawer 114 and held in a predetermined position by a magnetic mount 116. FIG. 11 depicts that the drawer 114 includes a linear toothed track 118 that meshes with a spring-biased, viscous oil-dampened gear 120. When the drawer 114 is pulled out, the track 118 rotates the gear 120 and tensions the spring therein. The drawer 114 is then released and moves in the opposite direction of the arrow A due to the restoring force of the spring. This return released movement of the drawer 114 is slowed due to the viscous oil and prevents the gemstone from being jarred from its predetermined upright position.

Figure 9:
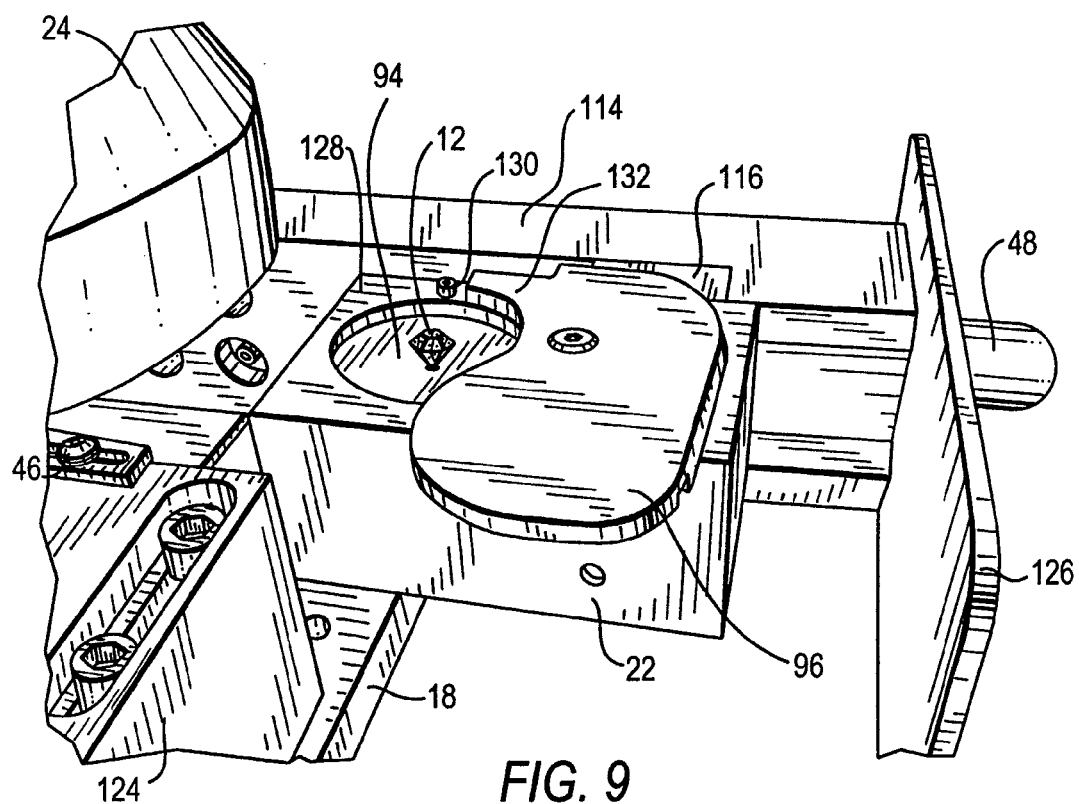
FIG. 9 is a broken-away, perspective view of the gemstone holder of FIG. 7 during closure of the drawer of the arrangement of FIG. 1.

During the return movement of the drawer 114, the gem holder 22 approaches the overhead annular support 24 and eventually is positioned in a loaded position directly thereunder, as shown in FIG. 3. Just prior to being positioned in the loaded position, the lid 96 is unlatched and released to its open position, as depicted in FIG. 9. This is accomplished by mutual abutment between a release member 146 mounted on a side block 124 and the release 122 on the holder 22. When the release member 146 abuts the release 122 during the return movement of the drawer 114, the lock 142 is disengaged from the shoulder 138, and the lid 96 is automatically opened under the force of the spring 106. The gemstone 12 is not disturbed from its predetermined upright position during the opening of the lid 96, since the gemstone passes with clearance along the curved recess 144.

As previously mentioned, the controller 80 processes the backlit and the frontlit images, to determine the aforementioned symmetry and/or coverage properties of the gemstone 12. As an initial step, the controller 80 energizes the backlight 30 and processes the backlit image, which resembles a circular dark region of interest for a round cut gemstone, analyzes the silhouette or shape, fills in any bright areas within the dark region of interest, rotates the dark region of interest (only if it is non-circular), determines the perimeter and the area of the dark region of interest, and counts the number of total pixels within the area of the gemstone.

Figure 12:
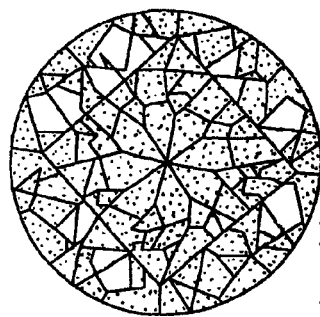
FIG. 12 is a backlit image of the gemstone taken in accordance with this invention.

Coverage is advantageously determined by processing the backlit image, as depicted in FIG. 12, and counting the number of total pixels within an area of the gemstone as described above, counting a number of coverage pixels having an intensity above a predetermined value in coverage regions of the backlit image within the area of the gemstone, and analyzing the number of coverage pixels compared to the number of total pixels to obtain a coverage ratio indicative of the percentage of light that is reflected. The higher the coverage ratio, the greater the coverage.

Optical symmetry, as distinguished from geometrical symmetry, is advantageously determined by processing each frontlit image of the return light, generating virtual images mirror symmetrical to the respective frontlit images, counting a number of symmetrical pixels common to each frontlit image and its respective virtual image within the area of the gemstone, and analyzing the counted number of symmetrical pixels compared to the number of total pixels as previously counted. More specifically, each frontlit image and its respective virtual image are juxtaposed, and the pixels of the juxtaposed images are compared. Intensity values are determined for the compared pixels, and their difference is determined. If each difference lies within a certain range, e.g., between zero and 10, then the compared pixels are deemed symmetrical. The number of the symmetrical pixels is then compared to the number of total pixels to obtain a symmetrical ratio for each set of frontlit and virtual images. All the symmetrical ratios are averaged to obtain a final symmetrical ratio. The higher the final symmetrical ratio, the greater the optical symmetry.

Figure 13:
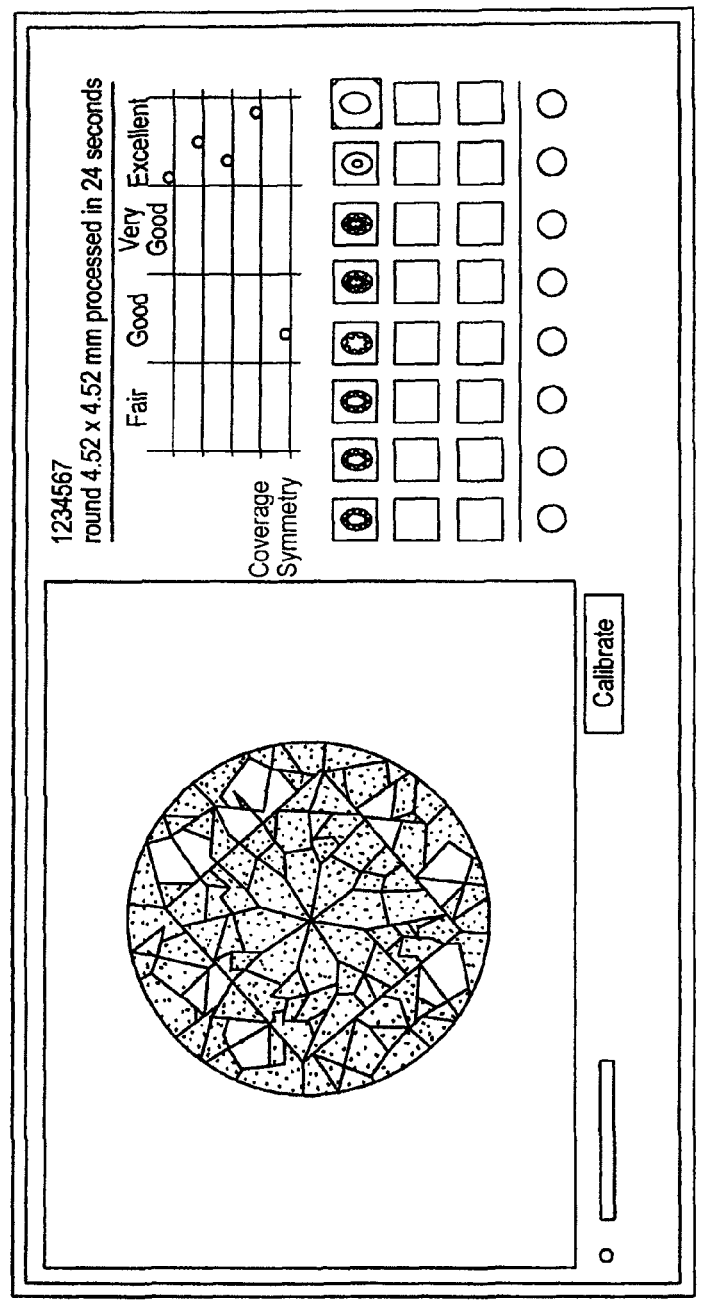
FIG. 13 is a display setting forth the coverage and symmetry properties of the gemstone examined in accordance with this invention.

Thus, the arrangement of this invention provides an objective, accurate and repeatable measure of symmetry and/or coverage properties of a gemstone essential for true price valuation of the gemstone. Other optical properties, such as contrast, fire, brilliance and scintillation can also be determined. FIG. 13 depicts an exemplary printout or certificate printed by the local printer 92 and depicting the symmetry and coverage properties in a line graph format, in which such designations as "fair, good, very good and excellent" are employed, rather than numerical percentages, for convenience. Other display formats could be employed. This measurement data can also be printed on a remote printer via the internet 90, or locally displayed on the monitor 88, or remotely displayed.

Figure 14:
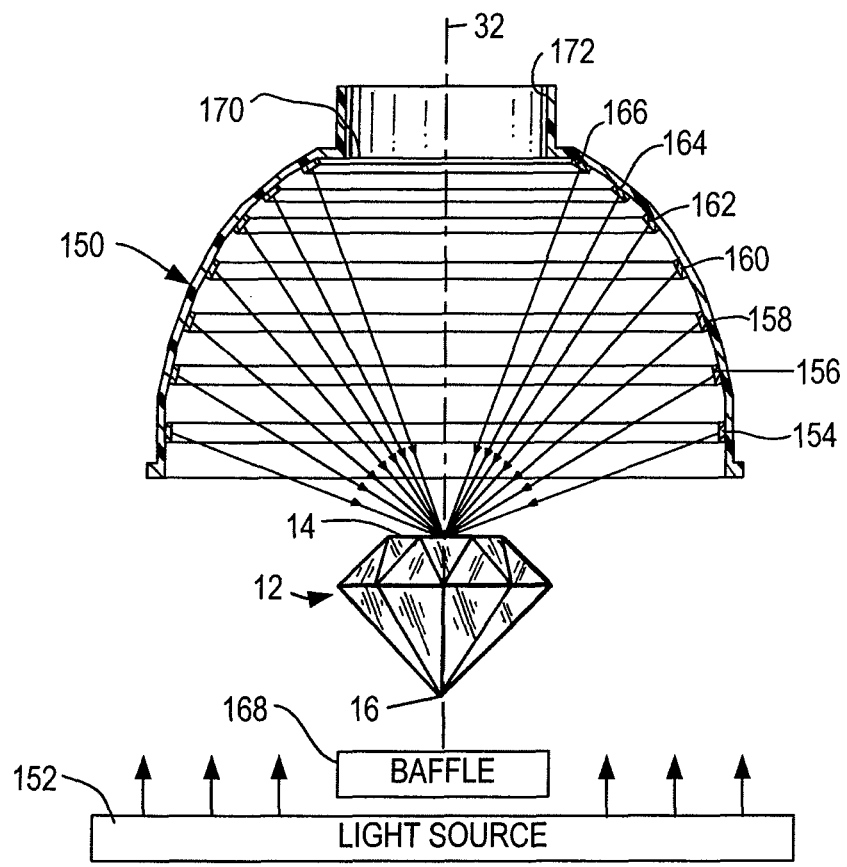
FIG. 14 is an enlarged, sectional view of another embodiment of an annular support analogous to that shown in FIG. 3, but operative for supporting a plurality of light reflectors facing a table of a gemstone, for use in the arrangement of FIG. 1.

As previously mentioned, FIG. 14 depicts an alternate embodiment, analogous to that shown in FIG. 3, for illuminating the uncovered table 14 of the gemstone 12. An annular hemispherical support 150 is spaced from a light source 152, for supporting a plurality of light reflectors 154, 156, 158, 160, 162, 164, and 166 of different reflectivity, e.g., different colors of the light spectrum, i.e., red, orange, yellow, green, blue, indigo and violet, and at different orientations and/or distances along the axis 32 away from the uncovered table 14 of the gemstone 12. Each light reflector is preferably arranged in an annulus around the axis 32, each annulus having a different diameter. More or fewer than the seven illustrated reflectors could be employed. The stationary light source 152, preferably a plurality of light emitting diodes lying in a plane, emits uniform light for reflection simultaneously from all the light reflectors as the light rays at the different orientations directly to the table 14 of the gemstone 12. A light baffle 168 blocks any light from the light source 152 from entering the gemstone from behind.

When the stationary light source 152 is energized, each annular light reflector reflects a light ray in an annular zone of generally uniform illumination and at a different wavelength, but at a different angular orientation relative to, as well as a different axial distance from, the gemstone 12. The support 150 has opposite openings 170, 172 through which light reflected off the gemstone passes en route to the imager, as described above. In a variant of the embodiment of FIG. 14, rather than reflectors, light-transmissive windows of different wavelengths can be employed.

It will be understood that each of the elements described above, or two or more together, also may find a useful application in other types of constructions differing from the types described above.

While the invention has been illustrated and described as embodied in an arrangement for, and a method of, examining a gemstone, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

We claim:

1. An arrangement for determining an optical property of a gemstone, comprising:
    a holder for holding the gemstone in an upright position in which a table of the gemstone is uncovered;
    an annular support bounding an interior and having a longitudinal axis, the annular support having an open passage extending along the axis through the annular support between opposite open ends;
    a plurality of annular frontlights stationarily mounted in the interior of the annular support, the annular frontlights being spaced apart along the axis and being concentric with the axis, the annular frontlights surrounding the open passage at different diameters and being remote from the open passage, the annular frontlights facing the uncovered table of the gemstone for directing light rays at different orientations to the uncovered table of the gemstone for return therefrom as return light;
    a stationary backlight for directing light toward a culet of the gemstone to illuminate the gemstone;
    an imager spaced away from the gemstone, and operative for imaging the return light through the open passage as a plurality of frontlit images, and for imaging the illuminated gemstone through the open passage as a backlit image; and
    a controller for sequentially energizing the annular frontlights along the axis to enable the imager to sequentially image the frontlit images along the axis, and for processing at least one of the frontlit and the backlit images to determine the optical property of the gemstone.

2. The arrangement of claim 1, wherein each annular frontlight comprises a multitude of energizable, light-emitting elements arranged in annular rows around the axis; and wherein the controller is operative for sequentially energizing the rows; and wherein the imager is operative for sequentially imaging the return light generated by the energized rows.

3. The arrangement of claim 1, wherein the annular frontlights comprise a plurality of annular light reflectors of different reflectivity; and wherein the controller energizes a light source to emit light for reflection from the light reflectors as the light rays at the different orientations to the uncovered table of the gemstone; and wherein the imager is operative for imaging the return light having different reflectivities.

4. The arrangement of claim 1, wherein the diameters of the annular frontlights increase in size along the axis toward the uncovered table of the gemstone.

5. The arrangement of claim 1, and comprising an optical assembly for capturing the return light and directing the return light through the open passage to the imager.

6. The arrangement of claim 1, and comprising a position adjuster for axially adjusting a position of the imager along the axis relative to the uncovered table of the gemstone.

7. The arrangement of claim 1, and comprising a support plate on which the holder, the annular support, the frontlights, the backlight, and the imager are commonly mounted; and comprising shock-absorbing mounts on the support plate for resisting shock forces.

8. The arrangement of claim 1, wherein the annular support is shaped as a dome, and wherein the open passage extends along the axis through the dome; and wherein the imager is positioned on the axis away from the dome.

9. The arrangement of claim 8, wherein the dome is spaced along the axis away from the uncovered table of the gemstone.

10. A method of determining an optical property of a gemstone, comprising:
   holding the gemstone in an upright position in which a table of the gemstone is uncovered;
   stationarily mounting a plurality of annular frontlights in an interior of an annular support having a longitudinal axis;
   configuring the annular support to have an open passage extending along the axis through the annular support between opposite open ends;
   arranging the annular frontlights to be spaced apart along the axis, to be concentric with the axis, to surround the open passage at different diameters, to be located remotely from the open passage, and to face the uncovered table of the gemstone for directing light rays at different orientations to the uncovered table of the gemstone for return therefrom as return light;
   directing light from a stationary backlight toward a culet of the gemstone to illuminate the gemstone;
   sequentially energizing the annular frontlights along the axis to sequentially image the return light through the open passage as a plurality of frontlit images along the axis;
   imaging the illuminated gemstone through the open passage as a backlit image; and
   processing at least one of the frontlit and the backlit images to determine the optical property of the gemstone.

11. The method of claim 10, wherein the processing is performed by processing the backlit image and counting a number of total pixels within an area of the gemstone, counting a number of coverage pixels having an intensity above a predetermined value in coverage regions of the backlit image within the area of the gemstone, and analyzing the number of coverage pixels compared to the number of total pixels to determine coverage of the gemstone.

12. The method of claim 10, wherein the processing is performed by processing the backlit image and counting a number of total pixels within an area of the gemstone, processing each frontlit image of the return light, generating virtual images mirror symmetrical to the frontlit images, counting a number of symmetrical pixels common to each frontlit image and its respective virtual image within the area of the gemstone, and analyzing the number of symmetrical pixels compared to the number of total pixels. to determine symmetry of the gemstone.

* * * * *